(12) United States Patent
Wang et al.

(10) Patent No.: US 9,278,980 B2
(45) Date of Patent: Mar. 8, 2016

(54) PROCESS OF MAKING DIFLUOROTHIENOTHIOPHENE BASED CONJUGATED POLYMERS

(71) Applicants: PHILLIPS 66 COMPANY, Houston, TX (US); SOLARMER ENERGY, INC., El Monte, CA (US)

(72) Inventors: Wei Wang, Arcadia, CA (US); Jun Yang, West Covina, CA (US); Chenjun Shi, La Puente, CA (US); Christopher Daeffler, Pasadena, CA (US); Janice Hawkins, Lake Forest, CA (US); Yue Wu, San Gabriel, CA (US); Ting He, Bartlesville, OK (US); Hui Huang, Beijing (CN); Amit Palkar, Bartlesville, OK (US); Kathy Woody, Bartlesville, OK (US); Joe Bullock, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 14/722,919

(22) Filed: May 27, 2015

(65) Prior Publication Data

US 2015/0344495 A1 Dec. 3, 2015

Related U.S. Application Data

(60) Provisional application No. 62/005,039, filed on May 30, 2014.

(51) Int. Cl.
 *C07D 495/04* (2006.01)
(52) U.S. Cl.
 CPC .................. *C07D 495/04* (2013.01)
(58) Field of Classification Search
 CPC .................................... C07D 495/04

USPC ........................................... 549/43
See application file for complete search history.

(56) References Cited

U.S. PATENT DOCUMENTS

| 8,436,134 | B2 | 5/2013 | Yu et al. |
|---|---|---|---|
| 8,653,228 | B2 | 2/2014 | Yu et al. |
| 8,703,960 | B2 | 4/2014 | Huang |
| 8,895,751 | B2 | 11/2014 | Huang |
| 2013/0056071 | A1 | 3/2013 | Palkar et al. |
| 2013/0214213 | A1 | 8/2013 | Wang et al. |
| 2014/0151657 | A1 | 6/2014 | Wang et al. |
| 2014/0221590 | A1 | 8/2014 | Woody et al. |
| 2015/0136224 | A1 | 5/2015 | Shi et al. |
| 2015/0210800 | A1 | 7/2015 | Wang et al. |

*Primary Examiner* — Taofiq A Solola
(74) *Attorney, Agent, or Firm* — Phillips 66 Company

(57) ABSTRACT

A method of producing a monomer wherein the method begins by dissolving 3-fluoro-4,6 dihydrothieno[3,4-b] thiophene in a solvent to create a solution. An initiator is then added to the solution to produce an initiated solution. This is followed by adding a fluorinated chemical to the initiated solution to produce 2,3-difluoro-4,6-dihydrothieno[3,4-b] thiophene. 2,3-difluoro-4,6-dihydrothieno[3,4-b]thiophene is then oxidized with an oxidant to produce 2,3-difluorothieno[3,4-b]thiophene. 2,3-difluorothieno[3,4-b]thiophene is then bromoated to produce 4,6-dibromo-2,3-difluorothieno[2,3-c]thiophene. The final step involves debrominating 4,6-dibromo-2,3-difluorothieno[2,3-c]thiophene and adding an aryl group to produce the monomer

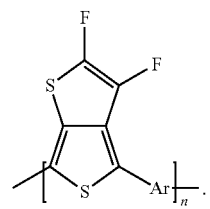

12 Claims, 1 Drawing Sheet

| Device Structure | Voc (V) | Jsc (mA/cm$^2$) | FF (%) | Median PCE (%) | PCE(%) |
|---|---|---|---|---|---|
| CS-38 | 0.88±0 | 11.60±0.09 | 61.96±0.49 | 6.33±0.03 | 6.36 |
| CS-39 | 0.83±0.01 | 11.76±0.16 | 62.31±0.81 | 6.06±0.11 | 6.18 |
| CS-40 | 0.74±0 | 14.12±0.16 | 67.39±1.07 | 7.04±0.05 | 7.12 |

PROCESS OF MAKING DIFLUOROTHIENOTHIOPHENE BASED CONJUGATED POLYMERS

CROSS-REFERENCE TO RELATED APPLICATIONS

This application is a non-provisional application which claims the benefit of and priority to U.S. Provisional Application Ser. No. 62/005,039 filed May 30, 2014, entitled "Process of Making Difluorothienothiophene Based Conjugated Polymers," which is hereby incorporated by reference in its entirety.

STATEMENT REGARDING FEDERALLY SPONSORED RESEARCH OR DEVELOPMENT

None.

FIELD OF THE INVENTION

This invention relates to the process of making difluorothienothiophene based conjugated polymers.

BACKGROUND OF THE INVENTION

Solar energy using photovoltaic effect requires active semiconducting materials to convert light into electricity. Currently, solar cells based on silicon are the dominating technology due to their high conversion efficiency. Recently, solar cells based on organic materials showed interesting features, especially on the potential of low cost in materials and processing. Judging from the recent success in organic light emitting diodes based on a reverse effect of photovoltaic effect, organic solar cells are very promising. Bulk hetero junction made from phase separated blends of semiconducting polymers and fullerenes is a popular structure that has been adopted for polymer solar cells.

There is a need in the art to manufacture polymer solar cells that exhibit increased solar conversion efficiency.

BRIEF SUMMARY OF THE DISCLOSURE

A method of producing a monomer wherein the method begins by dissolving 3-fluoro-4,6 dihydrothieno[3,4-b]thiophene in a solvent to create a solution. An initiator is then added to the solution to produce an initiated solution. This is followed by adding a fluorinated chemical to the initiated solution to produce 2,3-difluoro-4,6-dihydrothieno[3,4-b]thiophene. 2,3-difluoro-4,6-dihydrothieno[3,4-b]thiophene is then oxidized with an oxidant to produce 2,3-difluorothieno[3,4-b]thiophene. 2,3-difluorothieno[3,4-b]thiophene is then bromoated to produce 4,6-dibromo-2,3-difluorothieno[2,3-c]thiophene. The final step involves debrominating 4,6-dibromo-2,3-difluorothieno[2,3-c]thiophene and adding an aryl group to produce the monomer

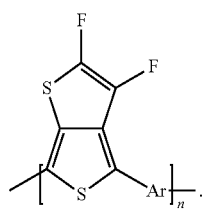

In an alternate embodiment, a method is described of producing a monomer wherein the method begins by dissolving 3-fluoro-4,6 dihydrothieno[3,4-b]thiophene in tetrahydrofuran in a non-oxygen atmosphere to create a solution. An initiator of n-butyllithium is then added to the solution to produce an initiated solution. This is followed by adding N-fluorobenzenesulfonimide to the initiated solution to produce 2,3-difluoro-4,6-dihydrothieno[3,4-b]thiophene. 2,3-difluoro-4,6-dihydrothieno[3,4-b]thiophene is then oxidized with meta-chloroperoxybenzoic acid to produce 2,3-difluorothieno[3,4-b]thiophene. 2,3-difluorothieno[3,4-b]thiophene is then bromoated with N-bromosuccinimide to produce 4,6-dibromo-2,3-difluorothieno[2,3-c]thiophene. The final step involves debrominating 4,6-dibromo-2,3-difluorothieno[2,3-c]thiophene and adding an aryl group to produce the monomer

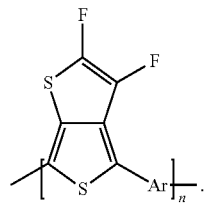

BRIEF DESCRIPTION OF THE DRAWINGS

A more complete understanding of the present invention and benefits thereof may be acquired by referring to the follow description taken in conjunction with the accompanying drawings in which:

FIG. 1 depicts the photovoltaic performance of various polymers.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

"Alkyl," as used herein, refers to an aliphatic hydrocarbon chains. In one embodiment the aliphatic hydrocarbon chains are of 1 to about 100 carbon atoms, preferably 1 to 30 carbon atoms, more preferably, 1 to 20 carbon atoms, and even more preferably, 1 to 10 carbon atoms and includes straight and branched chains such as methyl, ethyl, n-propyl, isopropyl, n-butyl, isobutyl, sec-butyl, t-butyl, n-pentyl, isopentyl, neopentyl, n-hexyl, and isohexyl. In this application alkyl group can include the possibility of substituted and unsubstituted alkyl groups.

"Alkoxy," as used herein, refers to the group R—O— where R is an alkyl group of 1 to 100 carbon atoms. In this application alkoxy groups can include the possibility of substituted and unsubstituted alkoxy groups.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

Aryl groups can be optionally substituted with one or with one or more Rx. In this application aryl groups can include the possibility of substituted aryl groups, bridged aryl groups and fused aryl groups.

The present embodiment describes a process of dissolving 3-fluoro-4,6-dihydrothieno[3,4-b]thiophene in a solvent to create a solution. An initiator is then added to the solution to produce an initiated solution followed by adding a fluorinated chemical to the initiated solution to produce 2,3-difluoro-4,6-dihydrothieno[3,4-b]thiophene. 2,3-difluoro-4,6-dihydrothieno[3,4-b]thiophene is then oxidized with an oxidant to produce 2,3-difluorothieno[3,4-b]thiophene. A brominating step then occurs to the 2,3-difluorothieno[3,4-b]thiophene to produce 4,6-dibromo-2,3-difluorothieno[2,3-c]thiophene. 4,6-dibromo-2,3-difluorothieno[2,3-c]thiophene is then debrominated and an aryl group is added to produce the monomer

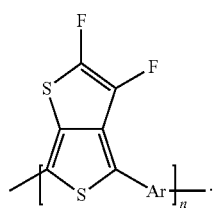

In this embodiment the solvent used could be tetrahydrofuran

In this embodiment the initiator used could be n-butyllithium

In this embodiment the fluorinated chemical is N-fluorobenzenesulfonimide.

In this embodiment the oxidant is meta-chloroperoxybenzoic acid.

In this embodiment the bromination occurs with N-bromosuccinimide.

The process describes a polymer that can have a monomer repeat unit comprising

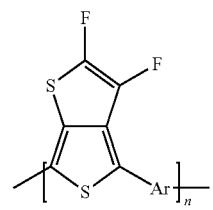

wherein Ar is an aryl group. It is theorized that the introduction of the fluorine atom can lower the polymer HOMO energy level and thus will lead to elevated open circuit voltage in photovoltaic devices. The fluorine atom is known to induce better planar molecular conformation in poly-thiophene systems. The formation of a difluorothienothiophene (DFTT) created similar results with better charge transport capability and higher short circuit current and fill factor.

In one embodiment, n ranges from 20 to 100, 2 to 1,000, 2 to 500 or even 2 to 200. In one embodiment, the monomer is used in a polymer. It is possible as a polymer that the polymer is either regio-regular or regio-random.

In one embodiment, Ar is

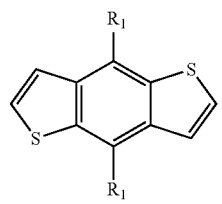

and R1 is independently selected from an alkyl group, an alkoxy group or an aryl aromatic group. As a polymer of this embodiment would have the monomer structure of

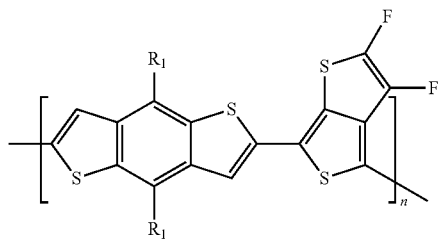

In another embodiment, Ar is

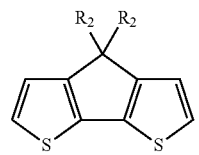

and R2 is independently selected from an alkyl group, an alkoxy group or an aryl aromatic group. As a polymer of this embodiment would have the monomer structure of

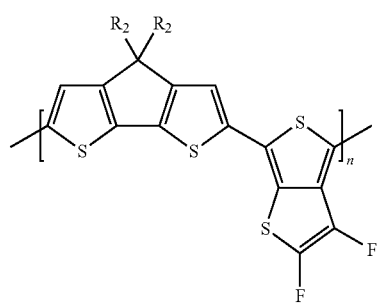

In yet another embodiment, Ar is

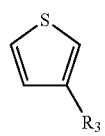

and R3 is independently selected from an alkyl group, an alkoxy group or an aryl aromatic group. As a polymer of this embodiment would have the monomer structure of

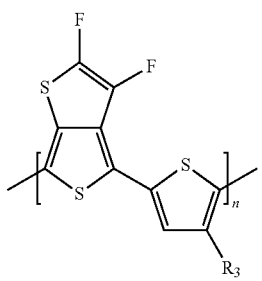

In another embodiment, Ar is

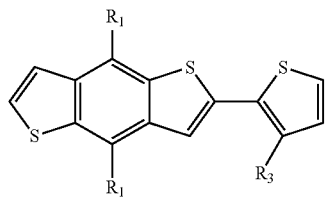

and R1 and R3 are independently selected from an alkyl group, an alkoxy group or an aryl aromatic group. As a polymer of this embodiment would have the monomer structure of

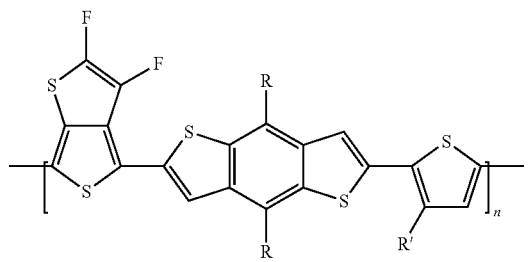

In another embodiment, Ar is

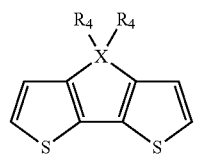

and R4 is independently selected from alkyl, alkoxy or aromatic substituents. In this embodiment X can be selected from any group 14 element. An example of possible group 14 elements includes C, Si and Ge. As a polymer of this embodiment would have the monomer structure of

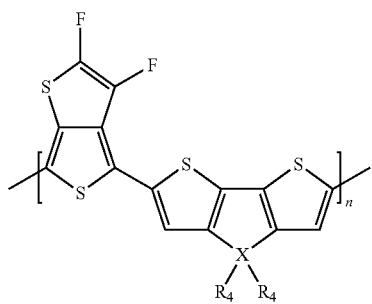

In yet another embodiment, Ar is

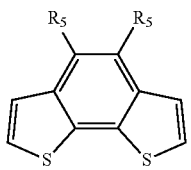

and R5 is independently selected from alkyl, alkoxy or aromatic substituents. As a polymer of this embodiment would have the monomer structure of

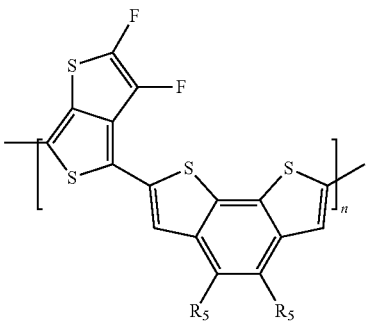

In yet another embodiment, Ar is

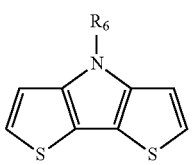

and R6 is independently selected from alkyl, alkoxy or aromatic substituents. As a polymer of this embodiment would have the monomer structure of

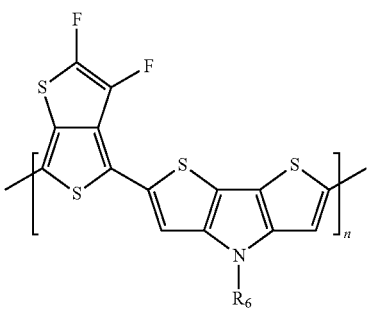

In yet another embodiment, Ar is

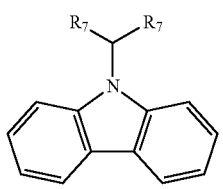

and R7 is independently selected from alkyl, alkoxy or aromatic substituents. As a polymer of this embodiment would have the monomer structure of

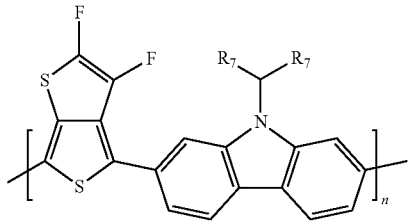

In another embodiment, Ar is

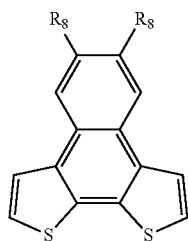

and R8 is independently selected from alkyl, alkoxy or aromatic substituents. As a polymer of this embodiment would have the monomer structure of

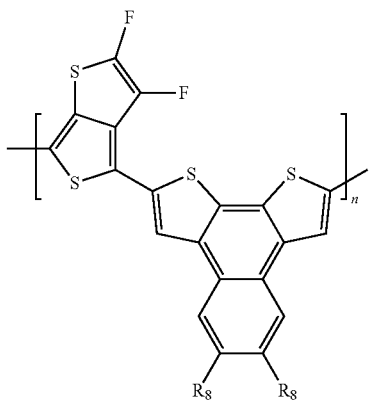

In another embodiment, Ar is

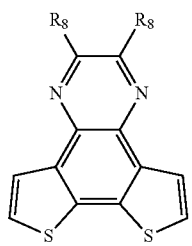

and R9 is independently selected from alkyl, alkoxy or aromatic substituents. As a polymer of this embodiment would have the monomer structure of

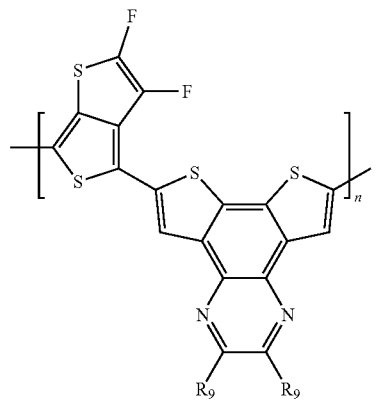

Synthesis:

The present embodiment describes a process of dissolving 3-fluoro-4,6-dihydrothieno[3,4-b]thiophene in a solvent to create a solution. An initiator is then added to the solution to produce an initiated solution followed by adding a fluorinated chemical to the initiated solution to produce 2,3-difluoro-4,6-dihydrothieno[3,4-b]thiophene. 2,3-difluoro-4,6-dihydrothieno[3,4-b]thiophene is then oxidized with an oxidant to produce 2,3-difluorothieno[3,4-b]thiophene. A brominating step then occurs to the 2,3-difluorothieno[3,4-b]thiophene to produce 4,6-dibromo-2,3-difluorothieno[2,3-c]thiophene. 4,6-dibromo-2,3-difluorothieno[2,3-c]thiophene is then debrominated and an aryl group is added to produce the monomer

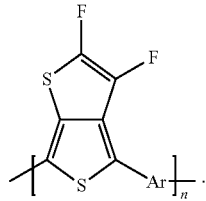

In this embodiment the solvent used could be tetrahydrofuran, diethyl ether or hexanes.

In this embodiment the initiator used could be n-butyllithium

In this embodiment the fluorinated chemical could be N-fluorobenzenesulfonimide.

In this embodiment the oxidant could be meta-chloroperoxybenzoic acid

In this embodiment the bromination could occur with N-bromosuccinimide.

Typically, the number average molecular weight of the polymers is in the range of approximately 1000 to 1,000,000, with ideal polymers having a number average molecular weight in the range of about 5000 to 500,000, and some ideal polymers having a number average molecular weight in the range of approximately 20,000 to 200,000. It will be appreciated that molecular weight can be varied to optimize polymer properties and the inventions of the present disclosure cover all molecular weights. For example, lower molecular weight can ensure solubility, while a higher molecular weight can ensure good film-forming properties.

The polymers produced from the present disclosure can be used as photovoltaic materials or active layer materials in electronic or photoelectric devices such as photodetector devices, solar cell devices, and the like. Photovoltaic devices, including solar cell devices, are generally comprised of laminates of a suitable photovoltaic material between a hole-collecting electrode layer and an electron-collecting layer. Additional layers, elements or a substrate may or may not be present.

EXAMPLES

Example 1

2,3-difluoro-4,6-dihydrothieno[3,4-b]thiophene

An oven-dried, 500 ml flask equipped with a magnetic stir bar was charged with 3-fluoro-4,6-dihydrothieno[3,4-b]thiophene (2.2 g, 13.75 mmol) and anhydrous THF (200 ml) under argon. The solution was cooled at −78° C. under a dry-ice acetone bath. N-butyllithium (2.5 M, 6.0 ml, 1.1 eq) was added dropwise. After cooling at −78° C. for half an hour, the reaction mixture was allowed to warm up to room temperature for 2 hours. The reaction vessel was recooled to −78° C. and $(PhSO_2)_2NF$ (4.8 g in 80 ml THF) was added dropwise. The mixture was warmed up to room temperature again for another 2 hours. After being quenched with 100 ml water, the organic phase was separated. The aqueous phase was extracted using $CH_2Cl_2$. The combined organic phase was dried over anhydrous sodium sulfate. After removal of the solvent, the white solid product was obtained by column chromatography (1.08 g, 44.1% GC-MS found m/q: 178; calculated for $C_6H_4F_2S_2$ 178.22)

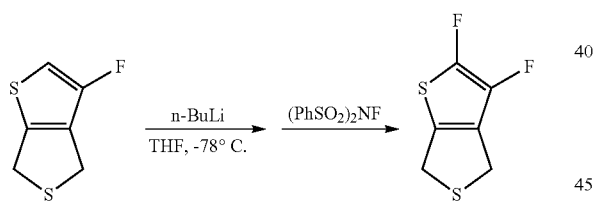

Example 2

2,3-difluorothieno[3,4-b]thiophene

An oven-dried 250 ml flask equipped with a magnetic stir bar was charged with 560 mg of 2,3-difluoro-4,6-dihydrothieno[3,4-b]thiophene (3.15 mmol) and 50 ml methylene chloride. The solution was cooled to 0° C. m-CPBA (0.71 g, 77%, 3.15 mmol) was added to one portion and the reaction mixture was allowed to warm up to room temperature overnight. The solvent was removed by a roto-vap and the residue was redissolved in 15 ml acetic anhydride and heated for 2 hours. The acetic anhydride was then removed by roto-vap and the product was purified by column chromatography to produce 199.5 mg of product. (GC-MS found m/q: 176 (Calculated for $C_6H_2F_2S_2$ 176.21)

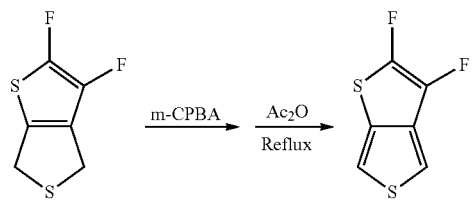 [SMILES: "Ac2O" ; Fc1sc2c(c1F)CSC2 ; "m-CPBA" ; "Reflux" ; Fc1sc2cscc2c1F]

Example 3

4,6-dibromo-2,3-difluorothieno[2,3-c]thiophene

DFTT 2,3-difluoro-4,6-dihydrothieno[3,4-b]thiophene (195 mg, 1.11 mmol) was dissolved in 10 ml for dry DMF. This solution was cooled at 0° C. In one portion, 592 mg NBS (3.0 eq) was added and the reaction mixture was stirred at 0° C. for 2 hours then warmed up to room temperature overnight. The reaction mixture was then poured into 5% $Na_2S_2O_3$ aqueous solution and extracted with methylene chloride. The organic layer was dried over $Na_2SO_4$. After removal of the solvent, the residue was purified by column chromatography to produce 198 mg (yield 53.5%) of a white solid product. (GC-MS found m/q: 334 (Calculated for $C_6Br_2F_2S_2$ 334.7)

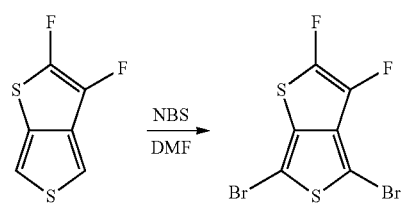

Example 4

CS-39

DFTT (50 mg, 0.150 mml) (and BDT8 (152 mg, 0.150 mmol) were dissolved in a mixture of toluene (5 ml) and DMF (1 ml). The reaction solution was sparged with Ar for 20 minutes $Pd(PPh_3)_4$ (6.9 mg, 4% mol) was added to the reaction mixture, then sparged with Ar for an addition 10 minutes. The solution was heated to 110° C. overnight. The dark blue solution was precipitated into methanol (120 ml) and the solid was collected by filtration. The solid was then dissolved in chlorobenzene and allowed to pass through a short column (silica gel). After concentration by roto-vap, the polymer solution was precipitated into hexanes. The solid was collected by centrifugation and dried in vacuum. The product was a dark blue solid (114 mg, 88.45).

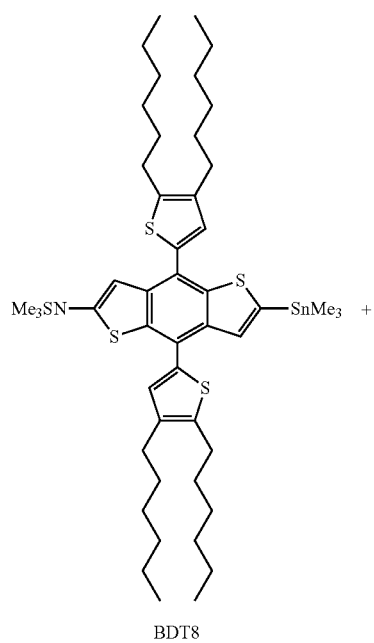

BDT8

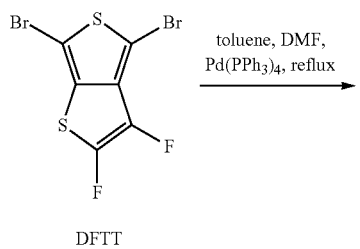

DFTT

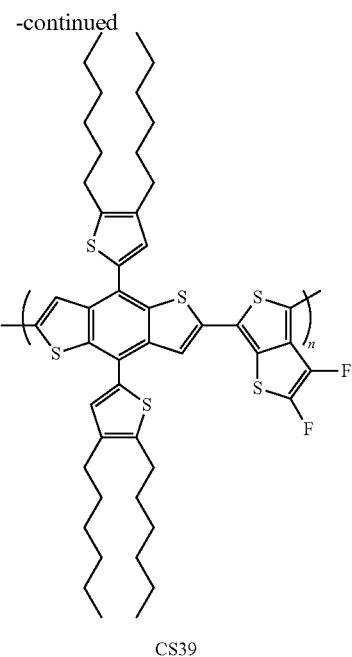

CS39

Example 5
CS-38

DFTT (45 mg, 0.135 mmol, 1.0 equiv), FTT-K1 (59.6 mg, 0.135 mmol, 1.0 equiv) and BDT8 (275 mg, 0.270 mmol, 2.0 equiv) were dissolved in a mixture of toluene (10 ml) and DMF (2 ml). The reaction solution was sparged with Ar for 20 minutes. Pd(PPh$_3$)$_4$ (11.0 mg, 4% mol) was added to the reaction mixture, then sparged with Ar for additional 10 minutes. The solution was heated to 110° C. overnight. The dark blue solution was precipitated into methanol (120 ml) and the solid was collected by filtration. The solid was then dissolved in chloroform and allowed pass through a short column (silica gel). After concentration by roto-vap, the polymer solution was precipitated into hexanes. The solid was collected by centrifugation and dried in vacuum. The product was a dark blue solid (112 mg, 45.2%).

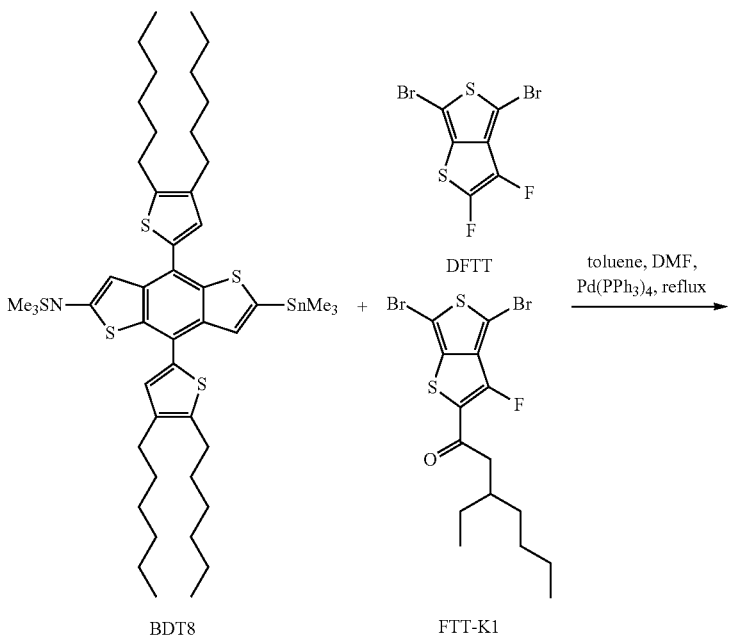

BDT8            FTT-K1

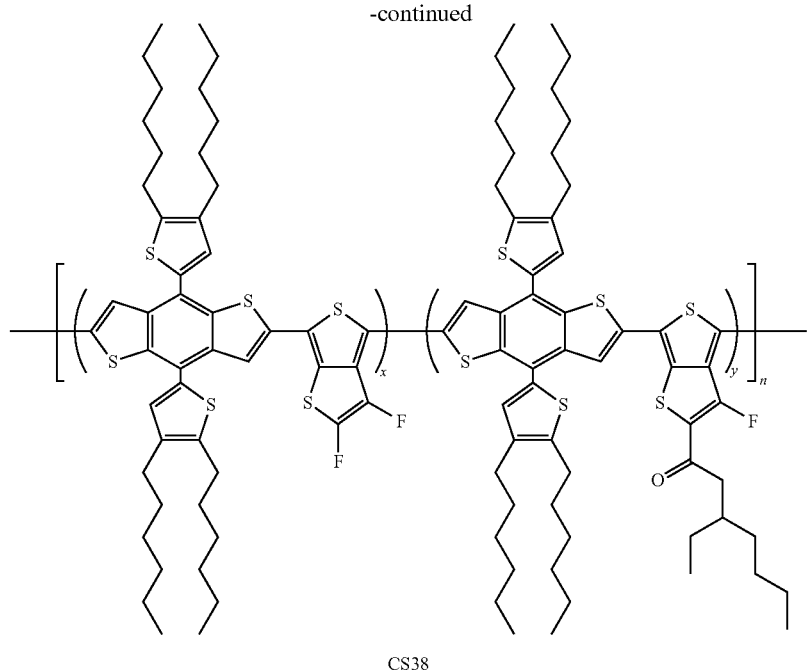

CS38

Example 6

CS-42

DFTT (30.3 mg, 0.091 mmol, 0.3 equiv), FTT-E (100.2 mg, 0.212 mmol, 0.7 equiv) and BDT (274 mg, 0.30 mmol, 1.0 equiv) were dissolved in a mixture of toluene (10 ml) and DMF (2 ml). The reaction solution was sparged with Ar for 20 minutes. Pd(PPh3)4 (14.0 mg, 4% mol) was added to the reaction mixture, then sparged with Ar for additional 10 minutes. The solution was heated to 110° C. overnight. The dark blue solution was precipitated into methanol (120 ml) and the solid was collected by filtration. The solid was then dissolved in chloroform and allowed pass through a short column (silica gel). After concentration by roto-vap, the polymer solution was precipitated into hexanes. The solid was collected by centrifugation and dried in vacuo. The product was a dark blue solid (238 mg, 92.6%).

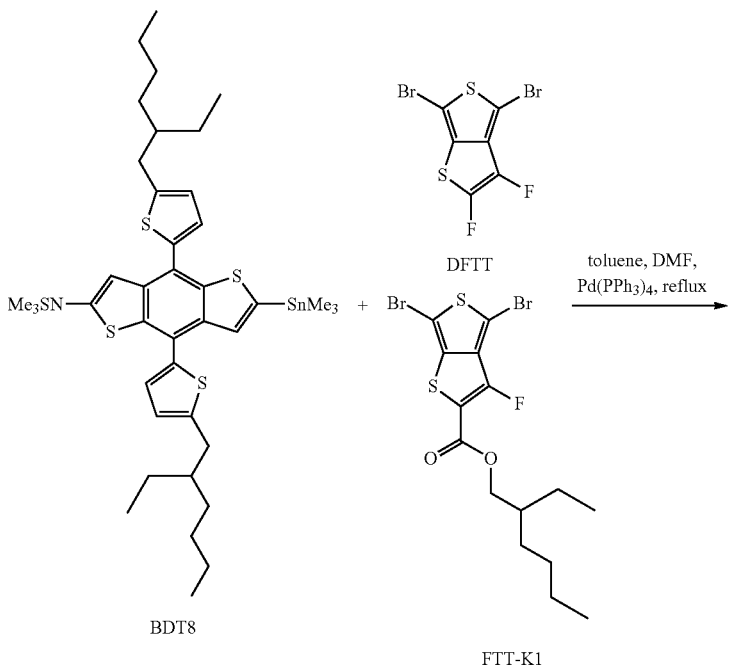

-continued

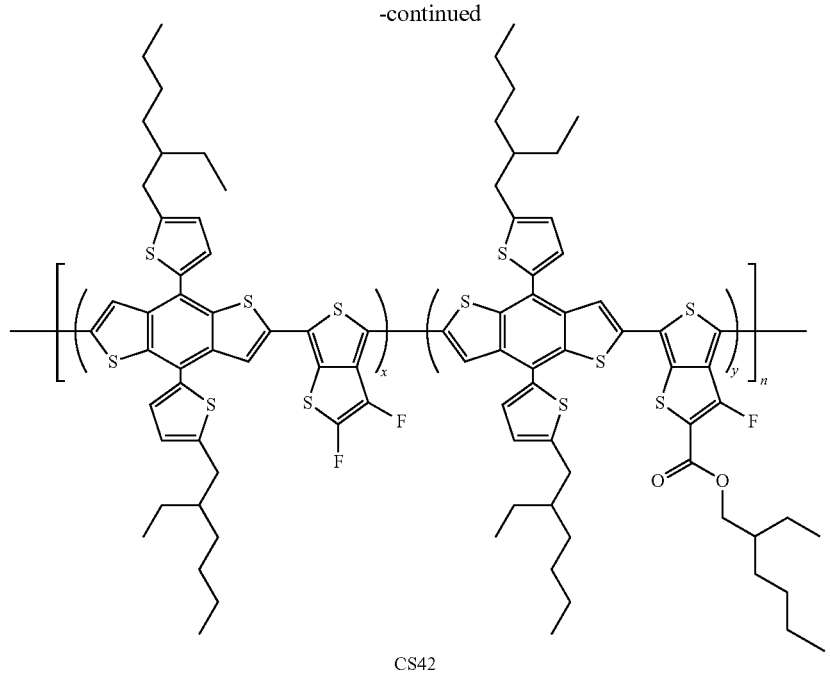

CS42

The photovoltaic properties of polymers CS38, CS39, and CS42 were investigated using a regular device structure (ITO/PEDOT:PSS/active layer/PFN/Al). The polymers CS38, CS39, CS42 and $PC_{70}BM$ were dissolved in o-xylene in a 1:1.6 (10 mg/mL:26 mg/mL, respectively) weight ratios. The solution was stirred at 70° C. overnight, and then filtered using a 2.7 μm glass fiber filter. Prior to use, a 2.5% volume ratio of 1,8-diiodooctane (purchased from Sigma Aldrich) was added to the solution. The solution was left to stir on the hotplate at 70° C. prior to use.

Regular structure fabrication: Indium Tin Oxide (ITO) patterned glass substrates were cleaned by sonication using the following solvents for each step: acetone, detergent water, deionized water, acetone, and isopropanol. Cleaned substrates were left to dry in the oven overnight. Poly(ethylenedioxythiophene):polystyrene sulphonate (PEDOT:PSS) was then spin-coated on ITO/glass substrates at 4000 rpm for 20 s and then annealed at 150° C. for 10 min. The active layer solution was then spin-coated on top of the PEDOT:PSS-coated ITO/glass substrates. The coated samples were left to vacuum for 1 hr. An electron transport layer (ETL) was deposited prior to electrode deposition. Thermal evaporation was used to deposit the electrode aluminum (800 Å). The samples were encapsulated prior to removing them from the glove box for testing. The devices with active area of 0.041 cm2 were tested using a 100 mW/cm2 (AM 1.5 G) solar simulator.

FIG. 1 depicts the photovoltaic performance of polymers CS38, CS39, and CS42 using regular device structure. The open-circuit voltage ($V_{OC}$) of CS38 is the highest at 0.88 V, which is significantly higher than CS39 (0.83 V) and CS42 (0.74 V).

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A method of producing a monomer comprising:
   dissolving 3-fluoro-4,6-dihydrothieno[3,4-b]thiophene in a solvent to create a solution, wherein the solvent is selected from the group consisting of: tetrahydrofuran, diethyl ether, hexane and combinations thereof;
   adding an initiator to the solution to produce an initiated solution;
   adding a fluorinated chemical to the initiated solution to produce 2,3-difluoro-4,6-dihydrothieno[3,4-b]thiophene;
   oxidizing 2,3-difluoro-4,6-dihydrothieno[3,4-b]thiophene with an oxidant to produce 2,3-difluorothieno[3,4-b]thiophene;
   brominating 2,3-difluorothieno[3,4-b]thiophene to produce 4,6-dibromo-2,3-difluorothieno[2,3-c]thiophene,
   debrominated 4,6-dibromo-2,3-difluorothieno[2,3-c]thiophene and adding an aryl group to produce the monomer

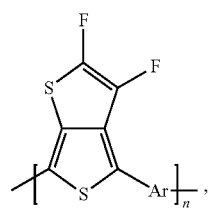

wherein the aryl group Ar is selected from the group consisting of:

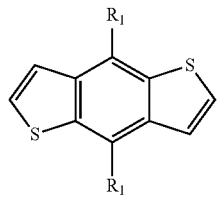

and R1 is independently selected from the group consisting of an alkyl group, an alkoxy group, an aryl group and combinations thereof,

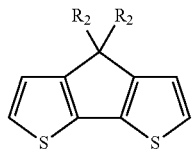

and R2 is selected from an alkyl group, an alkoxy group, an aryl group and combinations thereof,

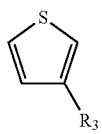

and R3 is selected from the group consisting of an alkyl group, an alkoxy group, an aryl group and combinations thereof, Ar is

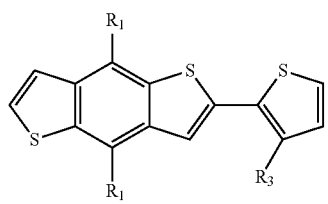

and R1 is selected from the group consisting of an alkyl group, an alkoxy group, an aryl group and combinations thereof and R3 is selected from an alkyl group, an alkoxy group, an aryl group and combinations thereof,

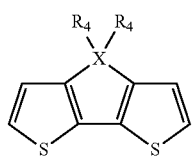

and R4 is selected from the group consisting of an alkyl group, an alkoxy group, an aromatic group and combinations thereof,

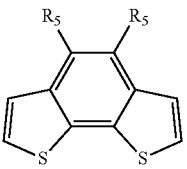

and R5 is selected from the group consisting of alkyl group, alkoxy group, aromatic group and combinations thereof, Ar is

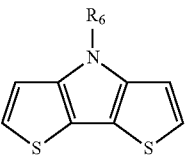

R6 is selected from the group consisting of an alkyl group, an alkoxy group, an aromatic group and combinations thereof,

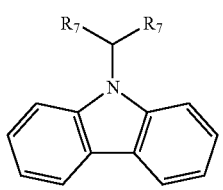

R7 is selected from the group consisting of an alkyl group, an alkoxy group, an aromatic group and combinations thereof,

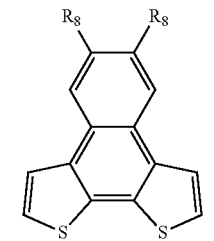

R8 is selected from the group consisting of an alkyl group, an alkoxy group, an aromatic group and combinations thereof,

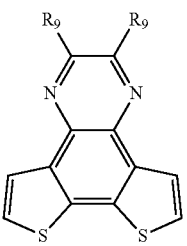

R9 is selected from the group consisting of an alkyl group, an alkoxy group, an aromatic group and combinations thereof.

2. The method of claim 1, wherein the initiator is n-butyl-lithium.

3. The method of claim 1, wherein the fluorinated chemical is N-fluorobenzenesulfonimide.

4. The method of claim 1, wherein the oxidant is meta-chloroperoxybenzoic acid.

5. The method of claim 1, wherein the bromination occurs with N-bromosuccinimide.

6. The method of claim 1, wherein the monomer is used in a polymer.

7. The method of claim 6, wherein the polymer n ranges from 20 to 100.

8. The method of claim 6, wherein the polymer is regioregular.

9. The method of claim 6, wherein the polymer is regiorandom.

10. The method of claim 6, wherein the polymer is used as photovoltaic material in one or more photovoltaic devices.

11. The method of claim 6, wherein the polymer is used as active layer material in one or more electronic devices.

12. A method of producing a monomer comprising:

dissolving 3-fluoro-4,6-dihydrothieno[3,4-b]thiophene in tetrahydrofuran in a non-oxygen atmosphere to create a solution;

adding n-butyllithium to the solution to produce an initiated solution;

adding N-fluorobenzenesulfonimide to the initiated solution to produce 2,3-Difluoro-4,6-dihydrothieno[3,4-b]thiophene;

oxidizing 2,3-difluoro-4,6-dihydrothieno[3,4-b]thiophene with thiophene meta-chloroperoxybenzoic acid to produce 2,3-difluorothieno[3,4-b]thiophene;

brominating 2,3-Difluorothieno[3,4-b]thiophene with N-bromosuccinimide to produce 4,6-dibromo-2,3-difluorothieno[2,3-c]thiophene, debrominated 4,6-dibromo-2,3-difluorothieno[2,3-c]thiophene and adding an aryl group to produce the monomer

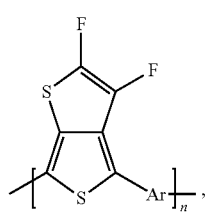

wherein the aryl group Ar is selected from the group consisting of:

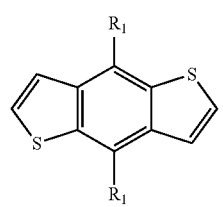

and R1 is independently selected from the group consisting of an alkyl group, an alkoxy group, an aryl group and combinations thereof,

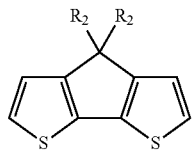

and R2 is selected from an alkyl group, an alkoxy group, an aryl group and combinations thereof,

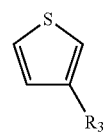

and R3 is selected from the group consisting of an alkyl group, an alkoxy group, an aryl group and combinations thereof, Ar is

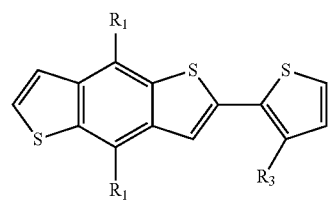

and R1 is selected from the group consisting of an alkyl group, an alkoxy group, an aryl group and combinations thereof and R3 is selected from an alkyl group, an alkoxy group, an aryl group and combinations thereof,

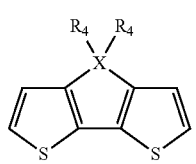

and R4 is selected from the group consisting of an alkyl group, an alkoxy group, an aromatic group and combinations thereof,

and R5 is selected from the group consisting of alkyl group, alkoxy group, aromatic group and combinations thereof, Ar is

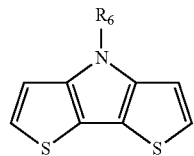

R6 is selected from the group consisting of an alkyl group, an alkoxy group, an aromatic group and combinations thereof,

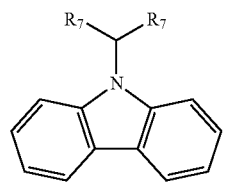

R7 is selected from the group consisting of an alkyl group, an alkoxy group, an aromatic group and combinations thereof,

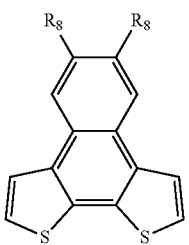

R8 is selected from the group consisting of an alkyl group, an alkoxy group, an aromatic group and combinations thereof,

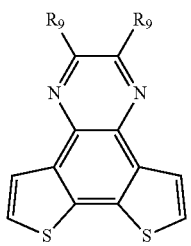

R9 is selected from the group consisting of an alkyl group, an alkoxy group, an aromatic group and combinations thereof.

* * * * *